United States Patent
Miyake et al.

(10) Patent No.: US 6,316,619 B1
(45) Date of Patent: Nov. 13, 2001

(54) POLYAMINOTRIAZINE AND ITS PRODUCTION AND USE

(75) Inventors: Kunihito Miyake, Nara; Kenji Kimura; Chikara Ohta, both of Osaka, all of (JP)

(73) Assignee: Sumitomo Chemical Company, Ltd., Osaka (JP)

( * ) Notice: Subject to any disclaimer, the term of this patent is extended or adjusted under 35 U.S.C. 154(b) by 0 days.

(21) Appl. No.: 08/889,895

(22) Filed: Jul. 8, 1997

(30) Foreign Application Priority Data

| Jul. 9, 1996 | (JP) | 8-179127 |
| Jul. 9, 1996 | (JP) | 8-179128 |
| Apr. 23, 1997 | (JP) | 9-105997 |
| Apr. 23, 1997 | (JP) | 9-105998 |

(51) Int. Cl.$^7$ .................. C07D 401/12; C07D 401/14
(52) U.S. Cl. .................................. 544/198; 252/405
(58) Field of Search .................. 544/198; 545/198

(56) References Cited

U.S. PATENT DOCUMENTS

| 4,086,204 | * | 4/1978 | Cassandrini et al. | 544/198 |
| 4,492,791 | * | 1/1985 | Orban et al. | 544/198 |
| 4,504,661 | * | 3/1985 | Wiezer | 544/198 |

OTHER PUBLICATIONS

JP–85–018450–stabilized macromolecule composition. Derwent Abstrct 86–248801, Jan. 2, 1985.*

* cited by examiner

Primary Examiner—Richard L. Raymond
Assistant Examiner—Venkataraman Balasubramanian
(74) Attorney, Agent, or Firm—Fitch, Even, Tabin & Flannery

(57) ABSTRACT

The present invention provides a polyaminotriazine represented by the formula (I):

$$Y-\underset{X^1}{N}C_6H_{12}\underset{X^2}{N}-\left[\begin{array}{c}N\\ \diagdown\diagup\\ \diagup\diagdown\\ N\quad N\\ |\\ Q\end{array}\right]-\underset{X^3}{N}C_6H_{12}\underset{X^4}{N}-Z \quad (I)$$

which has low melting point and good bleeding resistance, and is capable of being fed in a liquid form; a method for producing the polyaminotriazine; and a stabilized organic material comprising an organic material and the polyaminotriazine.

17 Claims, No Drawings

POLYAMINOTRIAZINE AND ITS PRODUCTION AND USE

BACKGROUND OF THE INVENTION

1. Field of the Invention

The present invention relates to polyaminotriazine and to methods for its production and use.

2. Background Information

A polyaminotriazine is known as a light stabilizer for organic materials such as polyethylene and polypropylene. One method which is known for its production is that of reacting dichlorotriazine with diamine in an amount of about 1 to 1.2 mol per mol of said dichlorotriazine in the presence of a base (JP-A-52-71486 and JP-B-4-4329, both of which are incorporated herein by reference).

However, since polyaminotriazine obtained by the above method has a high melting point, it is difficult to mix with an organic material by feeding in liquid form and therefore a powder form must be used. This creates problems in handling it in the working environment (e.g., clouds of dust arising during feeding) and in weighing the polyaminotriazine if a continuous feeding process is used.

Because of these problems, the present inventors have studied intensively in order to provide a polyaminotriazine having low melting point. As a result, it has been found that a polyaminotriazine which has a low melting point and can be fed in a liquid form can be obtained by reacting a specific dichlorotriazine with a specific diamine under specific conditions or reacting a specific dichlorotriazine and a specific monochlorotriazine with a specific diamine under specific conditions. It has also been found that the above-mentioned polyaminotriazine compound which is obtained by reacting a specific dichlorotriazine and a specific monochlorotriazine with a specific diamine has the advantageous characteristic that very little bleeding occurs when it is contained in an organic material. Thus, the present invention has been accomplished.

SUMMARY OF THE INVENTION

The present invention provides a polyaminotriazine represented by the formula (I):

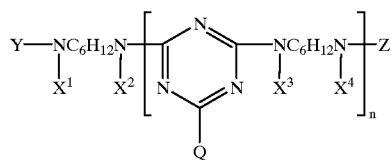

(I)

wherein
Q represents an alkyl amino group having 7 to 10 carbon atoms;

$X^1$, $X^2$, $X^3$ and $X^4$, which can be identical or different from one another, each represent a 2,2,6,6-tetramethyl4-piperidyl group or hydrogen, provided that at least one of $X^1$ and $X^2$ and at least one of $X^3$ and $X^4$ represent a 2,2,6,6-tetramethyl4-piperidyl group;

Y and Z, which can be identical or different from one another, each represent hydrogen or a 4,6-bis(1,1,3,3-tetramethylbutylamino)-1,3,5-triazin-2-yl group; and n, which is calculated from the number average molecular weight measured with gel permutation chromatography and converted as polystyrene, assuming that all of Y and Z are hydrogen in the calculation, represents a number of 3 or less, provided that, when both of Y and Z represent hydrogen, n is not more than 2.

The present invention also provides an excellent industrial method for producing the polyaminotriazine represented by formula (I) which comprises reacting dichlorotriazine represented by the formula (II):

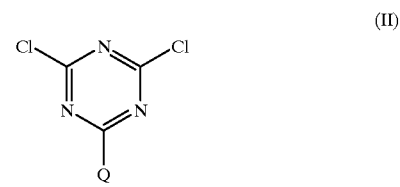

(II)

wherein Q is same as defined above, and monochlorotriazine represented by the formula (III):

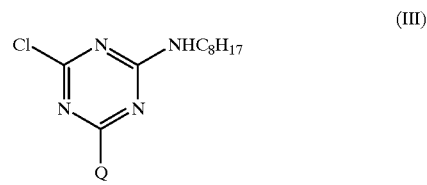

(III)

wherein Q is the same as defined above, in an amount of 10 mol or less per mol of dichlorotriazine (II) with diamine represented by the formula (IV)

X—NHC$_4$H$_{13}$NH—X$_5$ (IV)

in which X represents a 2,2,6,6-tetramethyl-4-piperidyl group and $X^5$ represents hydrogen or a 2,2,6,6-tetramethyl4-piperidyl group, in an amount of 0.5 to 2 mol per total mol of dichlorotriazine (II) and monochlorotriazine (III) in the presence of a base and an organic solvent, provided that, when the amount of monochlorotriazine (III) is 0.1 mol or less per mol of the dichlorotriazine (II), the amount of diamine (IV) is 1.3 to 2 mol per total mol of said dichlorotriazine (II) and said monochlorotriazine (III).

The present invention further provides a method of using the polyaminotriazine represented by the formula (I). Aspects of the invention have been described in Japanese patent applications 08-179128, filed Jul. 9, 1996, 08-179127, filed Jul. 9, 1996, 09-105998, filed Apr. 23, 1997, and 09-105997, filed Apr. 23, 1997, all of which are incorporated herein by reference.

DETAILED DESCRIPTION OF THE INVENTION

As "Q" in the formula (I), an octylamino group is preferred and particularly 1,1,3,3-tetramethylbutyl amino group is preferred.

The dichlorotriazine (II) and monochlorotriazine (III), which are used as starting material of the present invention, can be produced, for example, by reacting cyanuric chloride with an alkylamine having 7–10 carbon atoms according to the method described in JP-A-52-71486.

According to the method described in JP-A-52-71486, a mixture of the dichlorotriazine (II) and monochlorotriazine (III) can be obtained. The mixture may be used without further isolation. Alternatively, the dichlorotriazine (II) and monochlorotriazine (III) in the mixture may isolated and separated before being used for producing the polyaminotriazine of the present invention. The separated compounds may be further purified by a method such as recrystallization.

Examples of the dichlorotriazine (II) include 2,4-dichloro-6-(1,1,3,3-tetramethylbutylamino)-1,3,5-triazine, 2,4-dichloro-6-(n-octylamino)-1,3,5-triazine and mixtures thereof. Among these, 2,4-dichloro-6-(1,1,3,3-tetramethylbutylamino)-1,3,5-triazine is preferred.

Examples of the monochlorotriazine (III) include 2-chloro-4,6-bis(1,1,3,3-tetramethylbutylamino)-1,3,5-triazine, 2-chloro-4,6-bis(n-octylamino)-1,3,5-triazine and mixtures thereof. Among these, 2-chloro-4,6-bis(1,1,3,3-tetramethylbutylamino)-1,3,5-triazine is preferred.

The monochlorotriazine (III) is preferably used in an amount of 0.1 to 10 mol, more preferably 0.25 to 5 mol, per mol of the dichlorotriazine (II).

The diamine (IV), which is another raw material of the present invention, can be produced, for example, by reacting triacetoneamine with octylamine according to the method described in JP-A-64-50858, (which is incorporated herein by reference). The diamine (IV) can be used directly without further isolation, but is preferably isolated before use. The isolated diamine may be further purified by a purifying method such as distillation or recrystallization.

Examples of the diamine (IV) include N,N$^1$-bis(2,2,6,6-tetramethyl-4-piperidyl)hexamethylenediamine, N-(2,2,6,6-tetramethyl-4-piperidyl)hexamethylenediamine and mixtures thereof. It is particularly preferred to use the former alone or a mixture of the former and the latter wherein the amount of the latter is not more than ¼ mol per mol of the former as this results in polyaminotriazines which have much better performance characteristics as photostabilizers.

The diamine (IV) is used in an amount of about 0.5 to 2 mol, preferably about 1 to 2 mol, per mol of the total amount of the dichlorotriazine (II) and a monochlorotriazine (III), provided that, when monochlorotriazine (III) is not used, i.e., for producing a polyaminotriazine of formula (I) wherein Y and Z both represent hydrogen, the amount of diamine (IV) is from 1.3 to 2 per mol of the amount of the dichlorotriazine (II). When the amount is less than 0.5 mol or more than 2 mol, the resultant polyaminotriazine is liable to bleed from the organic material in which the polyaminotriazine mixture is contained. When the amount is less than 1.3 mol in the case of not using monochlorotriazine (III), polyaminotriazine having a high melting point is obtained, and the object of the present invention is thus not achieved.

The base is preferably an inorganic base. Examples of the inorganic bases include alkali metal hydroxides such as sodium hydroxide and potassium hydroxide, and alkali metal carbonates such as sodium carbonate and potassium carbonate. Among these, sodium hydroxide and potassium hydroxide are particularly preferred.

The base is normally used in an amount of about 1 to 3 times equivalent or greater based on the total equivalents of the dichlorotriazine (II) and monochlorotriazine (III), provided that, when monochlorotriazine (III) is not used, the amount of base is normally from 2 to 3 equivalents, preferably 2.2 to 2.5 equivalents. When the amount of the base used is less than 1 equivalent in the case of monochlorotriazine (III), or less than 2 equivalents when monochlorotriazine (III) is not used, the reaction may not be complete. On the other hand, even when the amount used exceeds 3 equivalents, little additional effect occurs from the excess, and it is therefore not economical.

The organic solvent may be any one which is inert to the reaction, and is not specifically limited. An organic solvent which is immiscible with water, is preferred. Among these, an aromatic solvent is more preferred.

Examples of aromatic solvents include toluene, xylene, ethylbenzene, mesitylene, o-dichlorobenzene and mixtures thereof. Among these, xylene and ethylbenzene are particularly preferred.

The amount of organic solvent used in the reaction is normally about 0.1 to 5 parts by weight, preferably about 0.2 to 1.5 parts by weight per one part by weight of the diamine (IV), provided that, in the case of producing a polyaminotriazine of formula (I) wherein Y and Z both represent hydrogen, the amount of the organic solvent is normally about 0.1 to 20 parts by weight, preferably about 0.5 to 10, parts by weight, per one part by weight of the dichlorotriazine (II).

The reaction is normally carried out at a temperature of not less than 140° C., preferably 140 to 220° C., more preferably 155 to 180° C. When the reaction is carried out at a temperature of less than 140° C., the rate of the reaction is slow and a long time is required to complete the reaction. The reaction can be carried out at normal pressure, elevated pressure or reduced pressure, and it is preferable to remove the water which is generated as the reaction progresses.

The resultant polyaminotriazine (I) can be isolated from the reaction mixture, for example, by washing the reaction mixture with water and optionally filtering and distilling off the low-boiling point fraction. Thus, the polyaminotriazine of formula (I) is obtained.

In order to reduce bleeding of the polyaminotriazine from the organic material, preferably at least 5%, more preferably at least 15%, and most preferably at least 50%, of Y and Z in the formula (I) should represent 4,6-bis(1,1,3,3-tetramethylbutylamino)-1,3,5-triazin-2-yl group.

At least one of $X^1$ and $X^2$ and at least one of $X^3$ and $X^4$ in the formula (I), respectively, represent a 2,2,6,6-tetramethyl-4-piperidyl group. It is preferred that at least 75 mol % of the sum total of $X^1$, $X^2$, $X^3$ and $X^4$ represent a 2,2,6,6-tetramethyl-4-piperidyl group.

The number "n" in the formula (I) is obtained from the number average molecular weight measured with gel permutation chromatography and converted as polystyrene, assuming that all of Y and Z are hydrogen. Carrying out the calculation to obtain "n" from the number average molecular weight, it is assumed that all of Y and Z are hydrogen, even if, in fact, Y and/or Z are not hydrogen. In formula (I), n represents a number of not more than 3, provided that, when both of Y and Z represent hydrogen, n is not more than 2. The number "n" is preferably from 0.2 to 3, more preferably 0.3 to 2, provided that, when both of Y and Z represent hydrogen, n is preferably from 0.2 to 2, more preferably 0.3 to 1.5. The gel permutation chromatogram is obtained by using UV detector.

When at least 5% of Y and Z in the formula (I) represent 4,6-bis(1,1,3,3-tetramethylbutylamino)-1,3,5-triazin-2-yl group, the maximum repetition number of the repeating unit of the polyaminotriazine (I), measured by a mass spectrometric analysis, is preferably 20 or less.

The polyaminotriazine mixture (I) of the present invention has a melting point making it suitable for feeding in liquid form, e.g., a melting point within the range of about 30 to 100° C.

Examples of the organic material which can be stabilized with the polyaminotriazine (I) of the present invention include the following:

(1) polyethylene, e.g., low-density polyethylene (LD-PE), high-density polyethylene (HD-PE), linear low-density polyethylene (LLD-PE), etc.

(2) polypropylene,
(3) ethylene/propylene copolymer,
(4) methylpentene polymer,
(5) EEA (ethylene/ethyl acrylate copolymer) resin,
(6) EVA (ethylene/vinyl acetate copolymer) resin,
(7) ethylene/vinyl alcohol copolymer resin,
(8) polystyrenes, e.g., polystyrene, poly(p-methylstyrene), poly( -methylstyrene), etc.,
(9) AS (acrylonitrile/styrene copolymer) resin,
(10) ABS (acrlonitrile/butadiene/styrene copolymer) resin,
(11) MS (special acrylic rubber/acrylonitrile/styrene copolymer resin,
(12) ACS (acrylonitrile/chlorinated polystyrene/styrene copolymer) resin,
(13) chlorinated polyethylene, polychloroprene, chlorinated rubber,
(14) polyvinyl chloride, polyvinylidene chloride,
(15) methacrylic resin,
(16) fluororesin,
(17) polyacetal,
(18) grafted polyphenylene ether resin and polyphenylene sulfite resin,
(19) polyurethane,
(20) polyamide,
(21) polyethylene terephthalate, polybutylene terephthalate,
(22) polycarbonate,
(23) polyacrylate,
(24) polysulfone, polyether ether ketone, polyether sulfone,
(25) aromatic polyester resin,
(26) epoxy resin,
(27) diallyl phthalate prepolymer,
(28) silicone resin,
(29) unsaturated polyester resin,
(30) acrylic modified benzguanamine resin,
(31) benzguanamine/melamine resin,
(32) urea resin,
(33) polybutadiene,
(34) 1,2-polybutadiene,
(35) polyisoprene,
(36) styrene/butadiene copolymer,
(37) butadiene/acrylonitrile copolymer,
(38) silicone rubber,
(39) epichlorohydrin rubber,
(40) acrylic rubber,
(41) natural rubber,
(42) chlorine rubber paint,
(43) polyester resin paint,
(44) urethane resin paint,
(45) epoxy resin paint,
(46) acrylic resin paint,
(47) vinyl resin paint,
(48) aminoalkyd resin paint,
(49) alkyd resin paint,
(50) nitrocellulose resin paint,
(51) oil paint,
(52) wax, and
(53) lubricating oil.

A mixture of the above-described organic materials can also be stabilized with the polyaminotriazine (I). The organic materials which can be stabilized with the polyaminotriazine (I) are not limited to those described above.

Among the organic materials mentioned above, polyethylenes such as low-density polyethylene (LD-PE), high-density polyethylene (HD-PE) and linear low-density polyethylene (LLD-PE) and synthetic resins such as polypropylene, EVA resin and ethylene/propylene copolymer are particularly suitable for being stabilized with the polyaminotriazine of the present invention.

The blending amount of the polyaminotriazine of the present invention with the organic material is normally about 0.01 to 5 parts by weight per 100 parts by weight of the organic material. If necessary, the organic material blended with this polyaminotriazine can contain other additives such as phenol antioxidant, sulfur antioxidant, phosphorous antioxidant, ultraviolet absorber, hindered amine photostabilizer other than the polyaminotriazine of formula (I), lubricant, plasticizer, halogen or phosphorous flame retardant, nucleating agent, metal deactivation agent, antistatic agent, pigment, inorganic filler, epoxy compound, absorption inhibiter and decoloring agent, as are customarily used in the art, and known to the skilled artisan. These additives and the polyaminotriazine of the formula (1) can be blended with the organic material simultaneously. Alternatively, the other additives and the polyaminotriazine can be blended at different stages.

When blending the polyaminotriazine of the formula (I) and other additives, which are optionally used, with the organic material, any known method and/or device can be used for obtaining a homogeneous mixture. For example, when the organic material is a solid polymer, the polyaminotriazine and any additives can be blended directly with the solid polymer. Alternatively, the polyaminotriazine and any additives can be blended in the form of a masterbatch with the solid polymer. (That is, the polyaminotriazine and other additives are blended together, optionally with a small amount of the solid polymer, and then subsequently added to the polymer.) When the organic material is a synthetic polymer, the polyaminotriazine and any additives can be blended in the form of a solution or a dispersion during the polymerization for producing the synthetic polymer or immediately after the polymerization. On the other hand, when the organic material is a liquid such as oil, the polyaminotriazine and any additives can be added directly and dissolved in the organic material. Alternatively, the polyaminotriazine and any additive can be dissolved or suspended in a liquid medium before addition to the organic material.

Thus, the present invention provides a polyaminotriazine (I) having a melting point making it suitable for feeding in a liquid form, e.g., about 30 to 100° C. In addition, the mixture is advantageous for practical use because of excellent bleeding resistance.

The following Examples further illustrate the present invention in detail but are not to be construed to limit the scope thereof. In the Examples, "parts" and "%" are by weight unless otherwise stated.

REFERENCE EXAMPLE 1

Xylene (200 g), water (80 g) and cyanuric chloride (80 g) were charged in a flask, and then 1,1,3,3-tetrabutylamine (57.2 g) and an aqueous 48% sodium hydroxide solution (37.6 g) were added thereto over 3 hours with stirring at 10° C.

After heating the mixture to 40° C., 1,1,3,3-tetramethylbutylamine (21.3 g) and an aqueous 48% sodium hydroxide solution (15 g) were added thereto over 30 minutes, followed by stirring at 40° C. for 1 hour.

After cooling to room temperature, the aqueous layer was separated to obtain 334 g of a xylene solution containing 0.17 mol of 2-chloro-4,6-bis-(1,1,3,3-tetramethylbutylamino)-1,3,5-triazine and 0.26 mol of 2,4-dichloro-6-(1,1,3,3-tetramethylbutylamino)-1,3,5-triazine.

EXAMPLE 1

$N,N^1$-bis(2,2,6,6-tetramethyl-4-piperidyl) hexamethylenediamine (231.3 g) and powdered sodium hydroxide (32.5 g) were charged in a flask equipped with a stirrer and a Dean-Stark trap, and then heated to 160° C. with stirring.

To this was added a xylene solution consisting of a mixed xylene (150 g) having the boiling point of 138–141° C. and 2,4-dichloro-6-(1,1,3,3-tetramethylbutylamino)-1,3,5-triazine (91.5 g) over 4 hours. Since the inner temperature began to decrease during the addition, a portion of the xylene was distilled off under reflux so that the inner temperature did not decrease to 160° C. or less. (During the reaction, xylene and water evaporated from the reaction mixture were condensed with a condenser. The condensed xylene and water were first trapped with a trap, a portion was removed, and the remainder returned to the reaction mixture.)

After completion of the addition, stirring was continued at the same temperature for 5 hours while removing distilled water, followed by cooling to room temperature. After having added water thereto and stirred, the aqueous layer was removed by separation and the organic layer was filtered. Then, the filtrate was concentrated by slight heating and vacuum drying to obtain 265 g of a solid.

This solid had a melting point of 41–44° C. The number average molecular weight measured with gel permutation chromatography and converted as polystyrene was 660, and "n" calculated from the number average molecular weight was 0.4.

EXAMPLE 2

A product was prepared in same manner described in Example 1 except that the amount of N,N$^1$-bis(2,2,6,6-tetramethyl-4-piperidyl)hexamethylenediamine was changed to 209.7 g, the amount of powdered sodium hydroxide was changed to 38 g, the amount of mixed xylene was changed to 175 g and the amount of 2,4-dichloro-6-(1,1,3,3-tetramethylbutylamino)-1,3,5-triazine was changed to 105.4 g. 244 g of a solid having a melting point of 78–83° C. was obtained. The number average molecular weight measured with gel permutation chromatography and converted as polystyrene was 865, and "n" calculated from the number average molecular weight was 0.8.

EXAMPLE 3

N,N$^1$-bis(2,2,6,6-tetramethyl-4-piperidyl)hexamethylenediamine (196.9 g) and powdered sodium hydroxide (43.3 g) were charged in a flask equipped with a stirrer and a Dean-Stark trap, and then heated to 160° C. with stirring.

To this was added the xylene solution (334 g) obtained in Reference Example 1 over 4 hours. Since the inner temperature began to decrease during the addition, a portion of the xylene was distilled off under reflux so that the inner temperature did not decrease to 160° C. or less, as described above.

Stirring was continued at the same temperature for 5 hours after completion of the xylene solution while removing distilled water, followed by cooling to room temperature. After having added water and stirred, the aqueous layer was removed and the organic layer was filtered. Then, the filtrate was concentrated to obtain 275 g of a solid.

This solid had a melting point of 63–70° C. The number average molecular weight measured with gel permutation chromatography and converted as a polystyrene was 699, and "n" calculated from the number average molecular weight was 0.52. The solid was subjected to a mass spectrometric analysis and it was calculated that a maximum molecular weight was 5783 and the maximum repetition number of the repeating unit was 9.

EXAMPLE 4

A product was prepared in the same manner as that described in Example 3 except that the xylene solution obtained in Reference example 1 was replaced with a xylene solution (325 g) containing 0.09 mol of 2-chloro-4,6-bis-(1,1,3,3-tetramethylbutylamino)-1,3,5-triazine and 0.34 mol of 2,4-dichloro-6-(1,1,3,3-tetramethylbutylamino)-1,3,5-triazine. 252 g of a solid was obtained.

This solid had a melting point of 90–96° C. The number average molecular weight measured with gel permutation chromatography and converted as polystyrene was 882, and "n" calculated from the number average molecular weight was 0.82. The solid was subjected to a mass spectrometric analysis, and it was calculated that a maximum molecular weight is 6974 and the maximum repetition number of the repeating unit was 11.

COMPARATIVE EXAMPLE 1

A product was prepared in the same manner as that described in Example 3 except that the amount of N,N-bis (2,2,6,6-tetramethyl-4-piperidyl)hexamethylenediamine was changed to 454 g, the amount of powdered sodium hydroxide was changed to 100 g and the xylene solution obtained in Reference example 1 was replaced with a xylene solution consisting of xylene (461 g) and 2,4-dichloro-6-(1,1,3,3-tetramethylbutylamino)-1,3,5-triazine (279 g). 620 g of a solid was obtained.

This solid had a melting point of 115–121° C. The number average molecular weight measured with gel permutation chromatography and converted as a polystyrene was 1819, and "n" calculated from the number average molecular weight was 2.4. The resulting solid was subjected to a mass spectrometric analysis and it was calculated that the maximum molecular weight was 9388 and the maximum repetition number of the repeating unit was 15.

EXAMPLES 5, 6, 7, 8 and COMPARATIVE EXAMPLES 2, 3, 4

(Evaluation of Weathering Properties)

To an unstabilized polyethylene resin (LLD-PE, 100 parts), the polyaminotriazine produced in Examples 2, 4 and Comparative example 1 and CYASORB UV-3346 (melting point 110–130° C., manufactured by Cytec Co.) were added. The mixture was granulated using an extruder at 200° C. and then formed into a film having a thickness of 20 μm using an inflation processing machine at 200° C. The resultant polyethylene film was spread outside and the weathering properties were evaluated by the number of days required to reduce a tensile elongation obtained by a tensile test to half of an initial value. The results are shown in Table 1.

TABLE 1

|  | Polyamino-triazine | Amount to be added (Parts by weight) | Half-life of tensile elongation (Days) |
| --- | --- | --- | --- |
| Example 5 | Example 2 | 0.1 | 100 |
| Example 6 | Example 2 | 0.2 | 135 |
| Example 7 | Example 4 | 0.1 | 100 |
| Example 8 | Example 4 | 0.2 | 130 |

TABLE 1-continued

|  | Polyaminotriazine | Amount to be added (Parts by weight) | Half-life of tensile elongation (Days) |
|---|---|---|---|
| Comparative example 2 | Comparative example 1 | 0.1 | 95 |
| Comparative example 3 | Comparative example 1 | 0.2 | 120 |
| Comparative example 4 | UV-3346 | 0.2 | 100 |

EXAMPLES 9, 10 AND COMPARATIVE EXAMPLE 5

(Evaluation of Bleeding Resistance)

To an unstabilized homopolypropylene resin (100 parts), calcium stearate (0.05 parts), tetrakis[methylene-3-(3,5-di-t-butyl-4-hydroxybutyl)propionate]methane (0.05 parts) and tris(2,4-di-t-butylphenyl)phosphite (0.05 parts) and the polyaminotriazine (0.2 parts) produced in Example 3, 4 and Comparative example 1 were added. The mixture was granulated using an extruder at 230° C. and then formed into a sheet having a thickness of 1 mm using an injection molder at 230° C.

The resultant sheet was put in an oven at 80° C. for 7 days and the bleeding resistance was evaluated by measuring the gloss value (600 specular gloss). The results are shown in Table 2. The gloss value was measured according to JIS K7105 (5.2). The higher the gloss value becomes, the better the bleed resistance. The results of Table 2 show that the compositions of the invention have a significantly improved gloss value over similar compositions which do not include the polyaminotriazines of the invention.

TABLE 2

|  | Polyaminotriazine | Gloss value |
|---|---|---|
| Example 3 | Example 1 | 94.8 |
| Example 4 | Example 2 | 89.2 |
| Comparative example 2 | Comparative example 1 | 75.6 |

What is claimed is:

1. A polyaminotriazine represented by the formula:

$$Y-NC_6H_{12}N\underset{X^1}{\overset{}{|}}\underset{X^2}{\overset{}{|}}\left[\begin{array}{c}N\\\parallel\\N\end{array}-NC_6H_{12}N\underset{X^3}{\overset{}{|}}\underset{X^4}{\overset{}{|}}\right]_n Z$$

with Q substituent wherein

Q represents an alkyl amino group having 7 to 10 carbon atoms;

$X^1$, $X^2$, $X^3$ and $X^4$, which may be identical or different from one another, each represent a 2,2,6,6-tetramethyl-4-piperidyl group or hydrogen, provided that at least one of $X^1$ and $X^2$ and at least one of $X^3$ and $X^4$ represent a 2,2,6,6-tetramethyl-4-piperidyl group, and wherein at least 75 mol % of the sum total of $X^1$, $X^2$, $X^3$ and $X^4$ represents a 2,2,6,6-tetramethyl-4-piperidyl group;

Y and Z, which may be identical or different from one another, each represent hydrogen or a 4,6-bis(1,1,3,3-tetramethylbutylamino)-1,3,5-triazin2-yl group; and n, which is calculated from the number average molecular weight measured with gel permeatation chromatography and converted as polystyrene, assuming that all of Y and Z are hydrogen in the calculation, represents a number less than or equal to 3, provided that, when both of Y and Z represent hydrogen, n is between about 0.3 and 1.5.

2. The polyaminotriazine according to claim 1, wherein Q is a group represented by the formula: —NHC$_8$H$_{17}$.

3. The polyaminotriazine according to claim 1, wherein at least 5% of Y and Z represent 4,6-bis(1,1,3,3-tetramethylbutylamino)-1,3,5-triazin-2-yl group.

4. The polyaminotriazine according to claim 1, wherein at least 15% of Y and Z represent 4,6-bis(1,1,3,3-tetramethylbutylamino)-1,3,5-triazin-2-yl group.

5. The polyaminotriazine according to claim 4, wherein at least 50% of Y and Z represent 4,6-bis(1,1,3,3-tetramethylbutylamino)-1,3,5-triazin-2-yl group.

6. The polyaminotriazine according to claim 1, wherein Y and Z both represent hydrogen.

7. The polyaminotriazine according to claim 6, wherein n is from about 0.2 less than 2.

8. The polyaminotriazine according to claim 1, wherein $C_6H_{12}$ represents a hexamethylene group.

9. The polyaminotriazine according to claim 1, wherein said polyaminotriazine has a melting point within the range of about 30 to 100° C.

10. The polyaminotriazine according to claim 1, wherein n is 0.2 to 0.82.

11. A method for producing the polyaminotriazine according to claim 1 which comprises:

reacting dichlorotriazine represented by the formula (II):

(II) — triazine ring with Cl, Cl, and Q substituents wherein Q is same as defined in claim 1, and monochlorotriazine represented by the formula (III):

(III) — triazine ring with Cl, NHC$_8$H$_{17}$, and Q substituents wherein Q is same as defined in claim 1, in an amount of 0.1 mol to 10 mol per mol of said dichlorotriazine (II) with a diamine represented by the formula (IV)

$$X-NHC_6H_{12}NH-X_5 \quad (IV)$$

in which X represents a 2,2,6,6-tetramethyl-4-piperidyl group and $X_5$ represents hydrogen or a 2,2,6,6-tetramethyl-4-piperidyl group, in an amount of 0.5 to 2 mol per mol of said dichlorotriazine (II) and said monochlorotriazine (III) in the presence of a base and an organic solvent, with the proviso that at least 75 mol % of the total of X and $X^5$ represent a 2,2,6,6-tetramethyl-4-piperidyl group.

12. The method according to claim 1, wherein the base is sodium hydroxide or potassium hydroxide.

13. The method according to claim 11, wherein the organic solvent is at least one selected from xylene and ethylbenzene.

14. The method according to claim 11, wherein the reaction is carried out at 140 to 220° C.

15. A method for producing the polyaminotriazine according to claim 1 which comprises:

reacting dichlorotriazine represented by the formula (II):

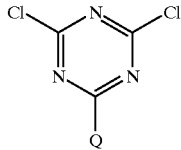

wherein Q is same as defined in claim 1 with a diamine represented by the formula (IV)

$$X—NHC_6H_{12}NH—X_5 \qquad (IV)$$

in which X represents a 2,2,6,6-tetramethyl-4-piperidyl group and $X_5$ represents hydrogen or a 2,2,6,6-tetramethyl-4-piperidyl group, in an amount of 1.3 to 2 mol per mol of said dichlorotriazine (II) in the presence of a base and an organic solvent, with the proviso that at least 75 mol % of the total of X and $X_5$ represent a 2,2,6,6-tetramethyl-4-piperidyl group.

16. A polyaminotriazine composition comprising a mixture of compounds represented by the formula (I):

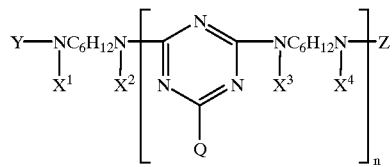

wherein the formula (I)

Q represents an alkyl amino group having 7 to 10 carbon atoms;

$X^1$, $X^2$, $X^3$ and $X^4$, which may be identical or different from one another, each represent a 2,2,6,6-tetramethyl-4-piperidyl group or hydrogen, provided that at least one of $X^1$ and $X^2$ and at least one of $X^3$ and $X^4$ represent a 2,2,6,6-tetramethyl-4-piperidyl group wherein at least 75 mol % of the sum total of $X^1$, $X^2$, $X^3$ and $X^4$ represents a 2,2,6,6-tetramethyl-4-piperidyl group;

Y and Z, which may be identical or different from one another, each represent hydrogen or a 4,6-bis(1,1,3,3-tetramethylbutylamino)-1,3,5-triazin-2-yl group;

a compound has a number of repeating units of greater than 0 and up to 20; and n is calculated from the number average molecular weight measured with gel permeation chromatography and converted as polystyrene, assuming that all of Y and Z are hydrogen, n represents the average number of repeating units, and n is less than or equal to 3, provided that, when both Y and Z represent hydrogen n is less than 2.

17. A polyaminotriazine composition according to claim 16, wherein at least 5% of Y and Z are 4,6-bis(1,1,3,3-tetramethylbutylamino)-1,3,5-triazin-2-yl groups.

* * * * *